US008986664B2

(12) United States Patent
DiColandrea et al.

(10) Patent No.: US 8,986,664 B2
(45) Date of Patent: Mar. 24, 2015

(54) USE OF MONOAMINE OXIDASE INHIBITORS TO IMPROVE EPITHELIAL BIOLOGY

(75) Inventors: Teresa DiColandrea, Cincinnati, OH (US); Robert Scott Youngquist, Mason, OH (US); Sancai Xie, Liberty, OH (US); Robert Lloyd Binder, Montgomery, OH (US); Gary Richard Fuentes, Batesville, IN (US); Deborah Lade, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/272,255

(22) Filed: Oct. 13, 2011

(65) Prior Publication Data

US 2012/0093752 A1 Apr. 19, 2012

Related U.S. Application Data

(60) Provisional application No. 61/393,489, filed on Oct. 15, 2010.

(51) Int. Cl.
*A61K 8/00* (2006.01)
*A61K 31/505* (2006.01)
(Continued)

(52) U.S. Cl.
CPC ........... *A61K 31/435* (2013.01); *A61K 8/40* (2013.01); *A61K 8/4926* (2013.01);
(Continued)

(58) Field of Classification Search
CPC ........... A61K 2300/00; A61K 31/138; A61K 2800/782; A61K 9/0014; A61K 31/135; A61Q 19/08; A61Q 7/00; A61Q 5/12; C07D 401/12; C07D 213/81

USPC ......... 424/70.1; 514/275, 354, 651, 654, 655, 514/657
See application file for complete search history.

(56) References Cited

U.S. PATENT DOCUMENTS 2,694,668 A 11/1954 Fricke
2,809,971 A 10/1957 Bernstein et al.
(Continued)

FOREIGN PATENT DOCUMENTS

EP 2033687 A1 3/2009
FR 2928545 A1 * 3/2008 ............... A61K 8/49
(Continued)

OTHER PUBLICATIONS

English translation of Michard et al. (FR 2 928 545 A1), Sep. 18, 2009, pp. 1-34.*
(Continued)

*Primary Examiner* — Aradhana Sasan
(74) *Attorney, Agent, or Firm* — Kelly L McDow

(57) ABSTRACT

The invention provides a method for improving hair biology, e.g., hair growth. The method comprises administering to a subject a monoamine oxidase inhibitor and a vasodilator, a zinc salt of a carboxylic acid, a xanthine compound, pyrithione or a salt thereof, saponin, tritapene, crataegolic acid, celastrol, asiatic acid, an inhibitor of 5-alpha-reductase, 1,4-methyl-4-azasteroid, an androgen receptor antagonist, azelaic acid or a derivate thereof, cyclosporin, triiodothyronine, diazoxide, retinoic acid, a prostaglandin analog, aminexil, carnitine tartrate, apigenin, procapil, or adenosine, in an amount effective to achieve a desired effect. The invention further provides a method of reducing or delaying the appearance of an age-related skin imperfection. The method comprises administering to the subject a composition comprising an MAO inhibitor. A kit for improving hair growth also is provided.

22 Claims, 4 Drawing Sheets

(51) Int. Cl.
  A61K 31/44     (2006.01)
  A61K 31/135    (2006.01)
  A61K 31/13     (2006.01)
  A61K 31/435    (2006.01)
  A61K 8/40      (2006.01)
  A61K 8/49      (2006.01)
  A61K 31/137    (2006.01)
  A61K 31/138    (2006.01)
  A61K 31/495    (2006.01)
  A61K 45/06     (2006.01)
  A61Q 7/00      (2006.01)
  A61Q 19/08     (2006.01)
  A61K 9/00      (2006.01)

(52) U.S. Cl.
  CPC ............ *A61K 8/4953* (2013.01); *A61K 31/137* (2013.01); *A61K 31/138* (2013.01); *A61K 31/495* (2013.01); *A61K 45/06* (2013.01); *A61Q 7/00* (2013.01); *A61Q 19/08* (2013.01); A61K 2800/782 (2013.01); A61K 9/0014 (2013.01)
  USPC .......... 424/70.1; 514/275; 514/354; 514/651; 514/654; 514/655

(56) References Cited

U.S. PATENT DOCUMENTS

| | | |
|---|---|---|
| 2,826,551 A | 3/1958 | Geen |
| 3,152,046 A | 10/1964 | Kapral |
| 3,236,733 A | 2/1966 | Karsten et al. |
| 3,753,196 A | 8/1973 | Kurtz et al. |
| 3,761,418 A | 9/1973 | Parran |
| 3,964,500 A | 6/1976 | Drakoff |
| 4,323,683 A | 4/1982 | Bolich, Jr. et al. |
| 4,345,080 A | 8/1982 | Bolich, Jr. |
| 4,364,837 A | 12/1982 | Pader |
| 4,379,753 A | 4/1983 | Bolich, Jr. |
| 4,470,982 A | 9/1984 | Winkler |
| 4,741,855 A | 5/1988 | Grote et al. |
| 4,885,107 A | 12/1989 | Wetzel |
| 5,104,646 A | 4/1992 | Bolich, Jr. et al. |
| 5,106,609 A | 4/1992 | Bolich, Jr. et al. |
| RE34,584 E | 4/1994 | Grote et al. |
| 7,144,584 B2 | 12/2006 | DiSanto |
| 7,524,505 B2 | 4/2009 | Lin et al. |
| 7,531,497 B2 | 5/2009 | Midha et al. |
| 7,585,827 B2 | 9/2009 | Geary et al. |
| 7,704,932 B2 | 4/2010 | Evans et al. |
| 7,709,015 B2 | 5/2010 | Masuda et al. |
| 7,727,516 B2 | 6/2010 | Botchkareva et al. |
| 7,754,240 B2 | 7/2010 | Staniforth et al. |
| 7,772,214 B2 | 8/2010 | Vatter et al. |
| 2001/0051657 A1* | 12/2001 | Chiang et al. ................. 514/562 |
| 2003/0021833 A1 | 1/2003 | Resnick |
| 2003/0223951 A1 | 12/2003 | Geary et al. |
| 2004/0241220 A1 | 12/2004 | DiSanto |
| 2004/0247888 A1 | 12/2004 | Watanabe et al. |
| 2006/0057075 A1 | 3/2006 | Arkin et al. |
| 2006/0067905 A1 | 3/2006 | Lintner et al. |
| 2008/0059313 A1 | 3/2008 | Oblong et al. |
| 2008/0206355 A1 | 8/2008 | Schwartz et al. |
| 2009/0069439 A1* | 3/2009 | Pertile .......................... 514/646 |
| 2009/0098096 A1 | 4/2009 | Mikhaleva et al. |
| 2010/0104646 A1 | 4/2010 | Kim |
| 2010/0247428 A1 | 9/2010 | Kim et al. |

FOREIGN PATENT DOCUMENTS

| | | |
|---|---|---|
| FR | 2928545 A1 | 9/2009 |
| GB | 849433 | 9/1960 |
| WO | WO-8800822 | 2/1988 |
| WO | WO-2008/027541 | 3/2008 |
| WO | WO 2008078905 A1 | 7/2008 |
| WO | WO-2010/086860 | 8/2010 |

OTHER PUBLICATIONS

International search report dated Mar. 5, 2012, 23 pages.

Edelstein et al., "Monoamine oxidases A and B are differentially regulated by glucocorticoids and "aging" in human skin fibroblasts", Cellular and Molecular Neurobiology, vol. 6, issue 2 (Jun. 1986), pp. 121-150, ISSN: 0272-4340 DOI: 10.1007/BF 00711066, Kluwer Academic Publishers—Plenum Publishers, New York.

Messenger et al., British Journal of Dermatology (2004), "Minoxidil: mechanisms of action on hair growth", vol. 150, issue 2, pp. 186-194.

Ko et al., Biochimica et Biophysica Acta (BBA), "Vasodilatory action mechanisms of apigenin isolated from *apium* graveolens in rat thoracic aorta", vol. 1115, issue 1, Nov. 14, 1991, pp. 69-74.

Stough et al., Mayo Clinic Proc., "Psychological effect, pathophysiology, and management of androgenetic alopecia in men", Oct. 2005, 80(10): pp. 1316-1322.

Moussa et al., British Journal of Pharmacology, "Monoamine oxidase: isoforms and inhibitors in Parkinson's disease and depressive illness", 2006, 147: pp. S287-S296.

* cited by examiner

USE OF MONOAMINE OXIDASE INHIBITORS TO IMPROVE EPITHELIAL BIOLOGY

CROSS REFERENCE TO RELATED APPLICATIONS

This reference claims the benefit of U.S. Application No. 61/393,489, filed Oct. 15, 2010, which is incorporated herein by reference.

FIELD OF THE INVENTION

The invention generally relates to methods of using monoamine oxidase inhibitors to improve the quality of hair and skin.

BACKGROUND OF THE INVENTION

Hair loss and skin appearance can have a profound effect on individuals' psychological well-being and quality of life. Anti-aging products represent a high percentage of skin and hair care product sales in the U.S. and abroad, and sales are expected to rise in many Western markets having an aging demographic. (Lennard, "Hair Care Growth Thinning for Near Term," Global Cosmetics Industry Magazine, May 2009.) Consumers seek these products to counteract age-related changes to epithelial biology that lead to skin imperfections (e.g., loss of elasticity, discoloration, dryness, and rough surface texture) and hair loss and thinning.

Thinning hair and significant hair loss, i.e., "baldness," is regarded in many cultures as less attractive. Hair growth is a cyclical process consisting of a growth stage (anagen), a regression stage (catagen), and a quiescent stage (telogen). During anagen, the hair bulb within the follicle penetrates the dermis and contacts the dermal papilla, triggering division of hair matrix keratinocytes. The new keratinocytes dehydrate and condense to form the hair shaft, which is pushed through the epidermis by newly dividing keratinocytes in the hair root. Hair growth ends in the catagen phase. The hair bulb separates from the dermal papilla, retracts from the dermis, and the follicle shrinks in size. In telogen, the hair remains attached to the follicle but, due to its shallow position in the epidermis, can easily be released from the skin. Normally, the follicle transitions back into anagen phase, during which the hair is pushed out of the follicle by hair newly formed by dividing keratinocytes. Disruption of the hair growth cycle leads to thinning and baldness. On the scalp, hair follicles shrink and shed terminal (long, pigmented) hair. The lost hair is either not replaced by new hair or is replaced by vellus (thin, short, non-pigmented) hair, resulting in the appearance of baldness.

The most common pharmacotherapeutics currently used to treat hair loss is minoxidil and 5-alpha reductase inhibitors, such as finasteride. The precise mechanism by which minoxidil reduces hair loss is unknown, and there is a significant percentage of patients that do not respond to therapy. While finasteride has been shown to slow hair loss in men, the drug is associated with several side effects, including gynecomastia and sexual dysfunction. Both minoxidil and anti-androgens can require several weeks to increase hair count, and must be continued indefinitely on a daily basis to maintain effectiveness.

Thus, there exists a need for materials and methods for reducing or delaying the effects of age on epithelial biology, particularly with respect to skin imperfections and hair loss.

SUMMARY OF THE INVENTION

The invention provides methods, compositions, and kits for improving epithelial biology and, in particular, reducing or delaying changes in hair and skin quality associated with age. In one aspect, the invention provides a method for improving hair growth in a subject. The method comprises administering to a subject a monoamine oxidase (MAO) inhibitor and a vasodilator in an amount effective to improve hair growth. In addition, the invention is directed to a method for improving hair biology, the method comprising administering to a subject (a) a MAO inhibitor and (b) one or more agents selected from the group consisting of a zinc salt of a carboxylic acid, a xanthine compound, pyrithione or a salt thereof, saponin, tritapene, crataegolic acid, celastrol, asiatic acid, an inhibitor of 5-alpha-reductase, 1,4-methyl-4-azasteroid, an androgen receptor antagonist, azelaic acid or a derivate thereof, cyclosporin, triiodothyronine, diazoxide, retinoic acid, a prostaglandin analogue, aminexil, carnitine tartrate, apigenin, procapil and adenosine, in an amount effective to improve hair biology in the subject.

Also provided is a method of reducing or delaying the appearance of an age-related skin imperfection in a subject. The method comprises topically administering to the subject a composition comprising an MAO inhibitor including, but not limited to, clorgiline, paragyline, lazabemide, selegiline, phenelzine, or rasagiline, in an amount effective to reduce or delay the appearance of an age-related skin imperfection. The composition does not comprise an iron chelator, an antiapoptotic agent, a neuroprotective agent, cholinesterase inhibitor, or an N-methyl-D-aspartic acid (NMDAR) receptor inhibitor.

The invention further provides a kit comprising a composition comprising a monoamine oxidase (MAO) inhibitor and, in the same composition or in a different composition, a vasodilator, in an amount effective to improve hair growth. The kit also comprises instructions for applying the composition(s) to the skin of a subject.

DETAILED DESCRIPTION OF THE INVENTION

Figure 1:
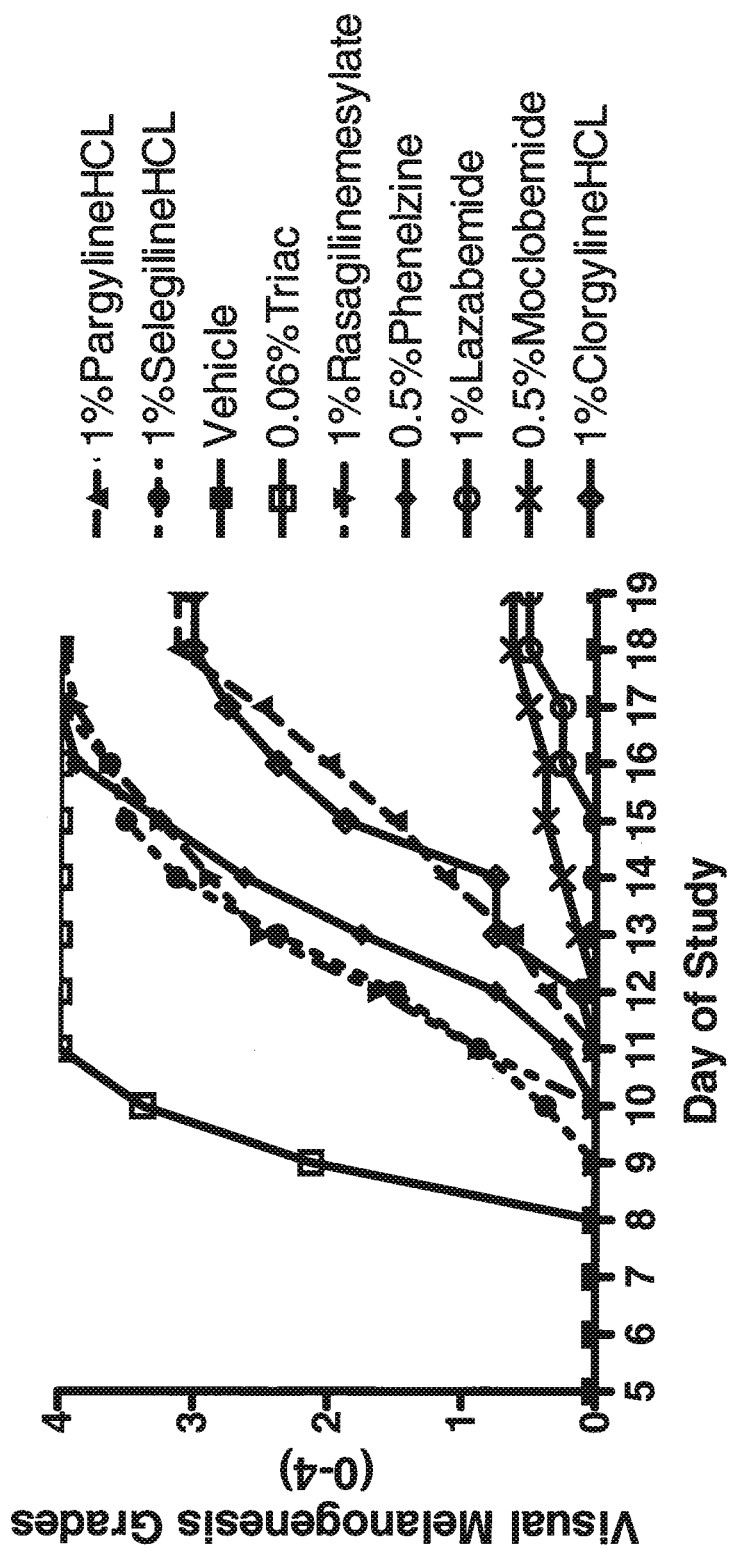
FIG. 1 is a line graph tracking hair growth (as estimated by visual melanogenesis grades (y-axis)) induced in a telogen conversion assay (TCA) by Triac, selegiline, paragyline, rasagiline, phenelzine, moclobemide, and lazabemide over a treatment period of 19 days (x-axis).

While the specification concludes with claims particularly pointing out and distinctly claiming the subject matter that is regarded as the invention, it is believed that the invention will be more fully understood from the following description taken in conjunction with the accompanying drawings.

All percentages and ratios used herein are by weight of the total composition and all measurements made are at 25° C., unless otherwise designated.

The invention is directed to compositions, kits, and methods for influencing epithelial biology to, e.g., improve hair biology and/or the condition or appearance of skin, by modulating the activity of monoamine oxidase (MAO). MAO (E.C.1.4.3.4) catalyzes the oxidative deamination of neurotransmitters. Two MAO isoforms have been identified, MAOA and MAOB, both of which metabolize dopamine, noradrenalin, adrenaline, tryptamine, and tyramine. MAOA also metabolizes serotonin, while MAOB preferentially metabolizes benzylamine and 2-phenylethylamine as substrates (Youdim & Bakhle, *British J. Pharmacology*, 147: S287-S296 (2006)). The invention is predicated, at least in part, on the discovery that MAO levels are increased in aged skin and regions of hair loss. The invention is further based, at least in part, on the discovery that MAO inhibitors, typically administered to treat neurological disease, can improve hair growth.

Improving Hair Biology

In one aspect, the invention provides a method for improving hair biology in a subject, the method comprising administering to a subject a MAO inhibitor and a second active agent that improves hair biology. As used herein, "improving hair biology" encompasses improving hair growth, reducing hair loss, preventing or reducing dandruff, increasing hair diameter, enhancing hair strength, enhancing hair shine, and/or enhancing hair curl, but is not meant to encompass modifying hair pigmentation. The method described herein also is suitable for maintaining hair biology, i.e., delaying hair loss, hair thinning, brittleness, and dullness. In some embodiments, the hair is scalp hair, eye brows, facial hair and/or eye lashes.

In one embodiment, the invention provides a method for improving hair growth in a subject. The method comprises administering to a subject a monoamine oxidase (MAO) inhibitor and a vasodilator in an amount effective to improve hair growth. As used herein, "improving hair growth" refers to increasing hair count or hair density on a region of the body, increasing the percentage of terminal hair in a region of the body, accelerating the onset of hair growth, and/or increasing the rate at which hair is generated. In one aspect, the method induces anagen in resting follicles. In this regard, in some instances, the method shortens the telogen phase of the hair growth cycle to promote new hair growth on a subject. Surprisingly, administration of a MAO inhibitor and a vasodilator, e.g., minoxidil, enhances hair growth in subjects to a greater degree than treatment with the MAO inhibitor or vasodilator alone. In one aspect, the improvement in hair growth is greater than that anticipated from the additive effect of the MAO inhibitor and vasodilator alone, i.e., administration of the MAO inhibitor and vasodilator achieves a synergistic effect.

Reversible and irreversible MAO inhibitors are suitable for use in the context of the invention. In one aspect, the inhibitor inhibits the activity of MAOB and, optionally, is selective for MAOB. Alternatively, the inhibitor inhibits the activity of MAOA and, optionally, is selective for MAOA, although non-selective inhibitors (i.e., inhibitors active against both MAOA and MAOB) also are contemplated for use in the invention. Thus, depending on the particular embodiment, the MAO inhibitor is an irreversible MAOA inhibitor, an irreversible MAOB inhibitor, a reversible MAOA inhibitor, a reversible MAOB inhibitor, an irreversible non-selective MAO inhibitor, or a reversible non-selective MAO inhibitor. Exemplary irreversible MAOB inhibitors comprise, e.g., a propargylyamine group, an indan group, a hydrazine group, phenylethylamine group, or a benzyl group. Many MAO inhibitors are known in the art, and others can be identified using, for example, the methods set forth in Tipton & Youdim, The assay of monoamine oxidase activity in *Methods in Biogenic Amine Research*, Elsevier, Amsterdam, Netherlands, pp. 441-467 (1983). Exemplary MAO inhibitors are set forth in Table A.

TABLE A

| Inhibitor | Selectivity | Mode of Action |
|---|---|---|
| Selegiline | MAOB | Irreversible |
| Rasagiline | MAOB | Irreversible |
| Clorygyline | MAOA | Irreversible |
| M30 | MAOA + MAOB | Irreversible |
| Ladostigil | MAOA + MAOB | Irreversible |
| Iproniazid | MAOA + MAOB | Irreversible |
| Phenelzine | MAOA + MAOB | Irreversible |
| Isocarboxazid | MAOA + MAOB | Irreversible |
| Tranylcypromine | MAOA + MAOB | Irreversible |
| Nialamide | MAOA + MAOB | Irreversible |
| Lazabemide | MAOB | Reversible |
| Moclobeminde | MAOA | Reversible |
| Brofaromine | MAOA | Reversible |
| Toloxatone | MAOA | Reversible |

In one aspect, the MAO inhibitor is selegiline, rasagiline, phenelzine, or pargyline. In another aspect, the inhibitor is lazabemide. In an alternative aspect, the MAO inhibitor is clorgiline. If desired, a derivative or metabolite of any of the aforementioned MAO inhibitors is used in the context of the invention so long as the derivative or metabolite improves hair biology. Administering combinations of two or more MAO inhibitors to improve hair biology, e.g., improve hair growth, or skin condition also is contemplated.

The method of improving hair growth further comprises administering to the subject a vasodilator, such as minoxidil, apigenin, hydralazine, prostaglandin, and prostacyclin. In one aspect, the method comprises administering to the subject a MAO inhibitor and minoxidil in amounts effective to improve hair growth. Surprisingly, subjects responsive to minoxidil experience improved hair growth in response to combination treatment compared to treatment with the vasodilator or MAO inhibitor, alone. Also surprisingly, MAO inhibitors potentiate the effectiveness of minoxidil in poor responders. A significant percentage of subjects do not respond, or are only minimally responsive, to minoxidil treatment alone. A "minimally responsive" subject experiences less than a 10% (e.g., 8%, 5%, or 3%) increase in target-area hair count following treatment with a vasodilator, e.g., minoxidil, for a period of from about two months to about a year (e.g., a treatment period of about three months, about four months, about six months, about nine months, or about twelve months) compared to matched subjects not administered minoxidil. The invention provides a method of improving hair growth (and/or reducing hair loss) in a subject that is not responsive or is minimally-responsive to vasodilator treatment alone, thereby expanding the patient population responsive to a vasodilator (e.g., minoxidil). Combination treatment with an MAO inhibitor and vasodilator also expands the type of hair loss that can be treated with minoxidil or other vasodilator.

In some instances, administering a vasodilator with a MAO inhibitor shown to be only moderately active for hair growth significantly improves a subject's response to treatment. For example, a particular MAO inhibitor (e.g., a reversible MAO inhibitor, such as lazabemide) may exhibit less hair growth activity but have other desirable properties such as, e.g., reduced side effects. Administering the MAO inhibitor with a vasodilator potentiates the therapeutic effect of the MAO inhibitor.

In one aspect, the method improves hair growth to a greater degree than administering the MAO inhibitor or vasodilator alone. In other words, hair growth resulting from the inventive method is superior to hair growth achieved using the MAO inhibitor or vasodilator alone. For example, administering an MAO inhibitor with a vasodilator induces the onset of new hair growth faster (i.e., reduces the lag time between initial treatment and appearance of new hair growth). In this regard, in some embodiments, combination treatment accelerates the onset of new hair growth by about 3%, about 5%, about 10%, about 15%, about 20%, or more when compared to treatment with either the vasodilator or MAO inhibitor alone. In other words, hair growth is observed earlier in the treatment period compared to the onset of hair growth observed in response to either the MAO inhibitor or vasodilator alone. Alternatively or in addition, treatment with both the MAO inhibitor and vasodilator results in a thicker (denser) region of hair or a region comprising more terminal hair than achieved with either compound alone.

Minoxidil was first introduced as a systemic treatment for hypertension, and is also known to be potassium channel opener (Stough et al., *Mayo Clin. Proc.*, 80(10), 1316-1322 (2005)). Thus, agents that open potassium channels and improve hair growth (or reduce hair loss) are also contemplated for use in the context of the invention.

In some instances, the subject is suffering from, or at risk of suffering from, hair loss or thinning Hair loss can be focal, i.e., limited to a particular region or pattern on the skin, or diffuse. Focal hair loss is most commonly associated with androgenetic alopecia, also known as male-pattern or female-pattern hair loss, which affects the vertex region of the skull. Other types of hair loss include anagen effluvium, telogen effluvium, alopecia greata, and scarring alopecia. While aging is a common cause of hair loss, hair loss or thinning also is caused by any of a number of medical conditions and environmental insults, such as loose anagen syndrome, tinia capitis, ichthyosiform erythroderma, leprosy, progeria, Siemens syndrome, hyperthyroidism, hypothyroidism, menopause, postpartum, autoimmune disorders, infection (e.g., ringworm, *Demodex folliculorum*), allergic reaction, cosmetic overprocessing, stress, nutritional deficiencies (e.g., resulting from anorexia), poisoning, burns, radiation, compulsive hair pulling or twisting, traction alopecia, and certain medications (e.g., antimitotics, retinoids, ACE inhibitors, lithium, anticonvulsants, anticoagulants, and chemotherapy). In some embodiments, the subject suffers from hair loss that is not associated with hereditary hair loss, such as androgenetic alopecia.

The invention further provides a method for improving hair biology, the method comprising administering to a subject (a) a monoamine oxidase (MAO) inhibitor and (b) one or more second active agents that, when administered in combination with an MAO inhibitor, improve hair biology. In one aspect, the second active agent is selected from the group consisting of a zinc salt of a carboxylic acid, a xanthine compound, pyrithione or a salt thereof, saponin, tritapene, crataegolic acid, celastrol, asiatic acid, an inhibitor of 5-alpha-reductase, 1,4-methyl-4-azasteroid, an androgen receptor antagonist, azelaic acid or a derivate thereof, cyclosporin, triiodothyronine, diazoxide, retinoic acid, a prostaglandin analogue, aminexil, carnitine tartrate, procapil, and adenosine. Administration of one second agent and administration of multiple second agents is contemplated. The MAO inhibitor and second agent are administered in an amount effective to improve hair biology.

As used herein, "xanthine compound" refers to one or more xanthines, derivatives thereof, and mixtures thereof. Exemplary xanthine compounds include, but are not limited to, caffeine, xanthine, 1-methyl xanthine, theophylline, theobromine, derivatives thereof, and mixtures thereof. In one embodiment, the composition comprises from about 0.1% to about 10% of a xanthine compound, in another embodiment from about 0.5% to about 5% of a xanthine compound, and in yet another embodiment from about 1% to about 2% of a xanthine compound. Alternatively or in addition, pyrithione or a salt of pyrithione, such as a polyvalent metal salt of pyrithione (e.g., zinc pyrithione), is administered as a second agent. Any form of polyvalent metal pyrithione salts may be used, including platelet and needle structures. Salts suitable for use herein include, e.g., those formed from the polyvalent metals magnesium, barium, bismuth, strontium, copper, zinc (e.g., the zinc salt of 1-hydroxy-2-pyridinethione (known as "zinc pyrithione" or "ZPT")), cadmium, zirconium and mixtures thereof, more preferably zinc. For example, in one embodiment, the second agent is ZPT in platelet particle form, wherein the particles have an average size of up to about 20 microns (e.g., up to about 5 microns or up to about 2.5 microns). Pyridinethione agents are further described, for example, in U.S. Pat. Nos. 2,809,971; 3,236,733; 3,753,196; 3,761,418; 4,345,080; 4,323,683; 4,379,753; and 4,470,982, and U.S. Patent Application Publication No. 2008/0206355.

In one aspect, the subject is a mammal, such as a male or female human. Alternatively, the subject is a fur- or hair-bearing non-human mammal. In this regard, veterinary and pet care applications also are contemplated wherein the subject is, for example, a canine (such as, but not limited to, a dog or a fox), feline, monkey, chimp, rodent (such as, but not limited to, a hamster, gerbil, rat, chinchilla, degu, or mouse), ferret, guinea pig, skunk, rabbit, bovine, or horse.

Improvements in hair biology are determined using any suitable technique, such as techniques known in the art for evaluating the efficacy of hair care products. For example, in one embodiment, the onset of new hair growth is evaluated by observing changes in hair count or density (number of hairs per predetermined area (e.g., $cm^2$)) or hair weight. Hair count protocols are known in the art and described in, for example, Olsen et al., *J. Am. Acad. Dermatol.*, 47: 377-385 (2002). Methods of evaluating improved hair growth and shine include, but are not limited to, global photograph assessments and subject self-evaluation. Similarly, visual inspection is used to detect increases in the amount of terminal hair and/or a reduction in vellus hair in a particular region of the body, which also signals improved hair growth. Hair loss also can be evaluated via visual inspection and self-evaluation. An additional exemplary method of monitoring hair loss comprises collecting and counting hair lost during the first morning combing or wash at various timepoints (e.g., at one week, four weeks, two months, three months, six months, nine months, or one year) during or following treatment. Hair count protocols are further described in, e.g., Wasko et al.,

*Arch. Dermatol.,* 144(6): 759-762 (2008). Any reduction in the amount of hair lost indicates an improvement in hair biology.

Examination of individual hairs is useful for identifying the hair growth phase of a follicle; anagen hairs comprise a sheath attached to the hair root, while telogen hairs lack a sheath. Other indicators of hair biology, such as hair diameter, curl, breakage, and shine, can be observed microscopically. Tensile strength, elasticity, and breakability also can be evaluated using a dynamometer, while glossmeters are suitable for evaluating hair shine, as described in, e.g., Velasco et al., *Br. J. Pharm. Sci.,* 45(1): 153-(2009). See also Robbins, *Chemical and Physical Behavior of Human Hair,* 4th Ed., Springer-Verlag, New York (2002). In some aspects, hair diameter is evaluated using, e.g., the Fiber Dimensional Analysis System (Mitutoyo, Model LSM 5000), or the imaging system described in Berger et al., British *Journal of Dermatology,* 149: 354-362 (2003).

In some aspects, the method prevents or reduces dandruff in the subject, such as dandruff caused by microbe-host interactions (e.g., dandruff caused by *Malassezia* yeasts). Reduction or prevention of dandruff can be determined by any suitable method, such as self-evaluation by the subject, global examination, or observing microbe levels on the affected area (see, e.g., Gemmer et al., *J. Clin. Microbiol.,* 40(9), 3350-3357 (2002)).

A complete recovery or maintenance of any of the hair biology parameters described herein is not required to achieve a desirable response. Indeed, any degree of improvement in hair biology (e.g., hair growth) confers a benefit to the subject. In some aspects, one or more parameters of hair biology is improved at least about 3%, at least about 5%, or at least about 10% (e.g., at least about 20%, at least about 30%, at least about 50%, at least about 70%, or at least about 90%) compared to the parameter prior to treatment, as measured on an untreated region of the body, or as compared to a matched negative control not subjected to the inventive method.

Improving and/or Maintaining Skin Condition

The invention further provides a method of reducing and/or delaying the appearance of one or more age-related skin imperfections in a subject. Without wishing to be bound by theory, the anti-aging skin benefits provided by the invention are consistent with the discovery of increased MAO levels in aged tissue, including photo-aged and intrinsically aged skin, and the discovery that MAO inhibition improves scalp condition. The method of reducing and/or delaying the appearance of one or more age-related skin imperfections comprises administering to the subject a composition comprising a MAO inhibitor in an amount effective to reduce or delay the appearance of an age-related skin condition. MAO inhibitors are described above and include, but are not limited to, clorgiline, paragyline, lazabemide, selegiline, phenelzine, or rasagiline. With respect to the method of reducing and/or delaying the appearance of one or more age-related skin imperfections, the MAO inhibitor is not a multi-functional compound described in International Patent Publication WO 2010/086860, and the composition administered to the subject does not comprise an iron chelator, an antiapoptotic agent other than the MAO inhibitor, a neuroprotective agent other than the MAO inhibitor, a cholinesterase inhibitor, or a N-methyl-D-aspartic acid (NMDAR) receptor inhibitor.

An "age-related skin imperfection" is an undesired skin condition or change in skin quality which manifests as part of the natural aging process and/or premature aging resulting from, e.g., sun exposure, alcohol use, lack of sleep, and tobacco use. Age-related skin imperfections include, but are not limited to, fine lines, fine wrinkles and course wrinkles; loss of elasticity or sagging; blotchiness, uneven pigmentation, and discoloration; age spots (areas of discrete pigmentation); enlarged pores; dryness; rough surface texture; translucency or thinness; fragility of the epidermis; impaired tissue repair; and loss of volume. The inventive method reduces the appearance the skin imperfection, thereby effecting a perceptible, positive change in skin appearance and feel. For example, in some embodiments, the method renders fine lines and/or wrinkles less noticeable, enhances skin hydration or suppleness, improves skin texture and smoothness (e.g., reduces scaliness), lessens discoloration, reduces the appearance of dark circles under the eyes, softens or smoothes the lips, improves skin color, increases skin volume and firmness, and/or improves skin elasticity. Alternatively or in addition, the method delays the appearance or progression of a skin imperfection, or prevents the skin imperfection. While the appearance of age-related skin imperfections are sometimes most noticeable on the face or neck, the inventive method is suitable for reducing or delaying the appearance of age-related skin imperfections on other regions of the body, such as hands, arms, elbows, legs, knees, feet, chest, torso, stomach, and back.

It will be appreciated that the skin imperfection need not be completely prevented or eradicated to achieve a desirable response. Any degree of improvement of one or more skin imperfections is contemplated. Similarly, any delay in the appearance of one or more age-related skin imperfections is encompassed by the invention. Methods for measuring improved skin quality are known in the art and include, for example, visual self evaluation by the subject, visual scoring by a panel of experts from photographs, methods of measuring skin moisture content (using, e.g., a skin hygrometer), and biopsies.

Compositions and Treatment Regimens

The MAO inhibitor (and, in some instances, a vasodilator or other second active agent) is administered to the subject in an amount effective to improve or maintain epithelial biology (e.g., reduce or delay the appearance of an age-related skin imperfection or improve hair biology). In many embodiments, the MAO inhibitor is topically administered to the subject. For example, the MAO inhibitor and, optionally, a second active agent, are applied topically to the target region of the body, e.g., the scalp. In instances where hair loss is localized, as with androgenetic alopecia, the MAO inhibitor and vasodilator can be administered to the balding patch (e.g., vertex region of the skull). Similarly, the MAO inhibitor may be applied directly to the face, neck, and/or hands to reduce or delay the appearance of age-related skin imperfections in those areas. In some instances, the MAO inhibitor (with or without the vasodilator or second active agent) is applied to hair follicles in the telogen phase.

An "effective amount" is an amount sufficient to achieve the desired biological effect. An effective amount of MAO inhibitor and, optionally, additional active agent(s) will vary with the particular condition being treated, the particular compound(s) used, the age and physical condition of the subject, and the duration of the treatment period. Similarly, the timing of administration of the MAO inhibitor and, in some embodiments, vasodilator or other second active agent, will depend upon the particular subject and the desired effect. It may be advantageous to administer multiple doses of an MAO inhibitor over a period of time (i.e., a "treatment period") to achieve a desired effect. For example, multiple doses of MAO inhibitor can be administered over a treatment period of, for example, about 1 month to about 24 months (e.g., about 3 months, about 6 months, about 9 months, about 12 months, about 15 months, about 18 months, or about 21 months), although longer treatment periods also are contemplated. In some instances, the MAO inhibitor is administered multiple times per week and/or multiple times a day during the treatment period. For example, in one embodiment, the MAO inhibitor is applied once or twice daily for one or more days per week (e.g., 2, 3, 4, 5, 6, or 7 days per week) for a period of time sufficient to achieve and/or maintain the desired results. When evaluating the effectiveness of a particular MAO inhibitor, vasodilator, second agent, and/or treatment regimen, one or more parameters of hair biology and/or skin biology is tested at one or more timepoints during the treatment period.

The initial application of the MAO inhibitor is preferably administered as soon as possible after it has been determined that a subject, such as a mammal (e.g., a human), is suffering from hair loss or at risk of suffering from hair loss. For example, the initial application is administered once hair loss is first observed or at the emergence of vellus hair at the balding area. In another aspect, the MAO inhibitor is administered concurrently with medical treatments carrying a risk of hair loss (e.g., chemotherapy or radiation therapy). In yet another aspect, the MAO inhibitor is administered when an age-related skin imperfection is noticed on a subject, or as a preventive measure prior to the appearance of an imperfection.

When applied topically, a composition as described herein is, some instances, left on the skin for a period of at least about 15 minutes, more preferably at least about 30 minutes, even more preferably at least about 1 hour, still more preferably for at least several hours, e.g., up to about 12 hours. The composition can be applied with the fingers or with an implement or device (e.g., pad, cotton ball, applicator pen, spray applicator, and the like). For example, the composition can be applied with a patch, which is useful, e.g., for skin areas needing intensive treatment. The patch can be occlusive, semi-occlusive or non-occlusive, and can be adhesive or non-adhesive. The composition can be contained within the patch or be applied to the skin prior to application of the patch.

In some embodiments of the invention, an MAO inhibitor is administered to a subject in conjunction with a second active agent, such as a vasodilator or an active agent that improves skin or hair biology (e.g., a zinc salt of a carboxylic acid, saponin, tritapene, crataegolic acid, celastrol, asiatic acid, an inhibitor of 5-alpha-reductase, 1,4-methyl-4-azasteroid, an androgen receptor antagonist, azelaic acid or a derivate thereof, cyclosporin, triiodothyronine, diazoxide, retinoic acid, a prostaglandin analogue, aminexil, carnitine tartrate, apigenin, procapil and adenosine). The second active agent is administered before, concurrently with, e.g., in combination with the MAO inhibitor in the same formulation or in separate formulations applied at substantially the same time, or after administration of the MAO inhibitor as described above. In one aspect, the inventive method comprises administering an MAO inhibitor and vasodilator (e.g., minoxidil) simultaneously to a subject, optionally, in a single composition. Alternatively or in addition, the MAO inhibitor and the second active agent are applied separately with a time delay between applications. For example, the MAO inhibitor is applied, e.g., 10 minutes, 30 minutes, one hour, six hours, or 12 hours after application of the second active agent, or vice versa. Both simultaneous and sequential application of the MAO inhibitor and second active agent is contemplated.

The invention further provides a composition comprising a MAO inhibitor and, optionally, one or more active agents for improving epithelial biology (e.g., improving hair biology and/or reducing or delaying one or more agent related skin imperfections). In one aspect, the invention provides a composition comprising a MAO inhibitor at a concentration of from about 0.1 wt. % to about 20 wt. %, by weight of composition. For example, the composition comprises from about 0.5 wt. % to about 10 wt. % (e.g., from about 1 wt. % to about 5 wt. %) MAO inhibitor, by weight of the composition. In one embodiment, the composition comprises about 1.5 wt. %, about 2 wt. %, about 2.5 wt. %, about 3 wt. %, about 3.5 wt. %, about 4 wt. %, or about 4.5 wt. %, MAO inhibitor, by weight of the composition. The invention further provides a MAO inhibitor composition described above that further comprises second active agent, such as a vasodilator (e.g., minoxidil). Alternative second active agents include, but are not limited to, a zinc salt of a carboxylic acid, saponin, tritapene, crataegolic acid, celastrol, asiatic acid, an inhibitor of 5-alpha-reductase, 1,4-methyl-4-azasteroid, an androgen receptor antagonist, azelaic acid or a derivate thereof, cyclosporin, triiodothyronine, diazoxide, retinoic acid, a prostaglandin analogue, aminexil, carnitine tartrate, apigenin, procapil, and adenosine. The concentration of each second active agent in the composition is, for example, about 0.01 wt. % to about 20 wt. %, by weight of the composition. For example, each active agent is present in the composition at a concentration of from about 0.1 wt. % to about 10 wt. % (e.g., from about 0.5 wt. % to about 5 wt. %), by weight of composition. In one embodiment, the composition comprises about 1 wt. % to about 3 wt. %, of each active agent, by weight of composition. As merely one example of the invention, a composition comprising one or more MAO inhibitors and minoxidil comprises about 2 wt. % or about 5 wt. % minoxidil.

The composition optionally further comprises one or more components known for use in hair care or personal care products, provided that the components are physically and chemically compatible with the MAO inhibitor and other active agents described herein, or do not otherwise unduly impair product stability, aesthetics or performance to form a personal care product.

In one aspect, the compositions described herein is formulated as, e.g., shampoo, conditioner, tonic, shower gel, liquid hand cleanser, facial cleanser, moisturizer, lotion (e.g., clarified lotion), skin lotion or cream (such as eye cream and/or lip cream), facial skin cosmetics (such as blusher and highlighter), eye cosmetics (such as eye shadow, eye brow color, and eye liner), lip cosmetics (such as lip rouge), foundation, concealer, wrinkle soothing serum, mascara, skin facial mask, sunscreen, scalp hair styling aid, facial hair styling aid, emulsion, oil, mousse, ointment, milk, pomade, solution, spray, aerosol, powder, foam, gel (such as skin gel, eye gel, and/or lip gel), serum, stick, paste, or other skin and hair products or treatment. In one embodiment, the composition is intended to be left on the skin and/or hair for some esthetic, prophylactic, therapeutic or other benefit (i.e., a "leave-on" composition).

Individual concentrations of additional components known for use in hair care or personal care may range from about 0.001 wt. % to about 10 wt. %, based on the weight of the personal care product. Non-limiting examples components that can be included in a personal care composition include: conditioning agents, cellulose or guar cationic deposition polymers, natural cationic deposition polymers, synthetic cationic deposition polymers, anti-dandruff agents, gel networks (e.g., fatty alcohol/surfactant networks), particles, suspending agents (such as suspending agents described in, e.g., U.S. Pat. Nos. 4,741,855 and RE34,584), paraffinic hydrocarbons, propellants, viscosity modifiers, dyes, non-volatile solvents, water soluble diluents, water insoluble diluents, opacifying agents, pearlescent aids, foam boosters, additional surfactants or nonionic cosurfactants, pediculocides, pH adjusting agents, perfumes, preservatives, chelants, proteins, skin active agents, sunscreens, UV absorbers, vitamins, amino acids, mono- or divalent salt, fragrance, skin conditioning agents, exfoliants, and mixtures thereof. Exemplary conditioning agents include, but are not limited to, organic conditioning oils, hydrocarbon oils, polyolefins, fatty esters, fluorinated conditioning compounds, fatty alcohols, alkyl glucosides and alkyl glucoside derivatives, quaternary ammonium compounds, polyethylene glycols, and silicone conditioning agents (e.g., silicone conditioning agents described in U.S. Reissue Pat. No. 34,584; U.S. Pat. Nos. 2,826,551; 3,964,500; 4,364,837; 5,104,646; and 5,106,609; British Patent No. 849,433; and *Silicon Compounds*, Petrarch Systems, Inc. (1984)). Non-limiting examples of suitable synthetic cationic deposition polymers are described in U.S. Patent Application Publication No. 2003/0223951. Exemplary anti-dandruff additives are described in, e.g., U.S. Pat. Nos. 2,694,668; 2,809,971; 3,152,046; 3,236,733; 3,753,196; 3,761,418; 4,345,080; 4,323,683; 4,379,753; 4,470,982; and 4,885,107. The composition of the invention also, in certain embodiments, contains a preservative system to inhibit microbiological growth and maintain the integrity of the product. Exemplary components of personal care compositions also are disclosed in, e.g., U.S. Pat. Nos. 7,772,214; 7,727,516; 7,709,015; 7,704,932; 7,585,827; and 7,531,497.

The invention further includes a kit comprising a composition comprising (a) a monoamine oxidase (MAO) inhibitor and, in the same composition or in a different composition, a vasodilator, in an amount effective to improve hair growth, and (b) instructions for applying said composition(s) to the skin of a subject. In one embodiment, the vasodilator is minoxidil. The composition(s) are presented in a container, such as a single dose or multidose vial, containing a dose of MAO inhibitor and/or vasodilator for administration. Alternatively, the composition is packaged into divided containers, such as a divided bottle or a divided foil packet, each comprising a single dose of active agent. Any container shape appropriate for delivering a pharmaceutical or cosmetic composition to a consumer is suitable for use in the context of the invention. Exemplary containers include, but are not limited to, a glass or plastic bottle, a glass or plastic jar, packet or pouch, a plastic or metal tube, or a blister pack with individual doses for administration according to a treatment schedule. Alternatively, the composition is impregnated onto a wipe or sponge for application to the skin Generally, the instructions will include a tangible expression describing the active agent concentration, as well as within certain embodiments, relative amounts of excipient ingredients or diluents (e.g., water, saline or PBS) that may be necessary to reconstitute or dilute the composition to a desired consistency.

The invention is further described in the following examples. The examples serve only to illustrate the invention and are not intended to limit the scope of the invention in any way.

EXAMPLES

Example 1

This example describes expression analysis of MAO in scalp and photo-aged skin

MAO expression and enzyme activity was studied in balding and non-balding human subjects. Higher levels of MAO gene expression also observed in balding individuals in comparison with non-balding individuals. In regions of balding scalp, MAOB levels were more about three-fold greater than MAOB levels observed in non-balding scalp, and were most pronounced in the vertex region compared to the occipital region. MAOB enzyme activity was observed in human hair-bearing skin. To confirm that MAOB correlates with reduced hair growth, MAOB production was studied in mice topically administered dihydrotestosterone (DHT), known to inhibit hair growth, and Triiodothyroacetic Acid (Triac), a hair growth inducer. MAOB levels increased greater than two fold in C57Bl/6 mice administered DHT (12.5 mg/day using a subcutaneous, continuous release pellet). Reduced MAOB levels were observed following administration of Triac (0.06%) in C3H mice. Thus, increased levels of MAOB correlate with hair growth inhibition and loss, while decreased MAOB levels correlate with hair growth.

MAO expression also was studied in intrinsically aged human skin and human skin exposed to light and ultraviolet (UV) radiation. Biopsies were taken from the buttocks and forearm of human volunteers grouped by age and skin phenotype (classified using the Fitzpatrick scale). Gene expression profiles from samples taken from young Caucasian individuals ("young group") and older Caucasian individuals ("aged group") were determined. Gene expression profiles from buttocks samples from each group were compared to study gene expression changes that are intrinsic to skin as it ages. The buttocks is an appropriate region for comparison because, at least for most individuals, the region is not exposed to UV radiation and the subjects in this study were selected to have no history of nude sunbathing. Expression profiles of forearm samples from each group were compared to study gene expression changes that occur over time in the presence of regular exposure to UV radiation and photodamage. Younger individuals are expected to experience less UV exposure compared to older individuals who, over the course of a lifetime, have been chronically exposed to UV and other extrinsic stressors. The older subjects were selected to have at least moderate photodamage on their forearms.

Examination of MAOB levels revealed that MAOB is upregulated in both intrinsic aging and in photoaging. MAOB expression was approximately 1.38-fold higher (with high statistical significance) in buttocks samples taken from the aged group compared to samples taken from the young group. In forearm skin, MAOB levels were about 1.83-fold greater (with high statistical significance) in samples taken from the aged group compared with samples taken from younger individuals. The increase in expression levels is significant in humans. Thus, MAOB levels increase in the skin with intrinsic age, and the increase is more pronounced with exposure to external stressors, such as UV radiation. In at least some instances, increased MAOB expression correlates with increased internal oxidative stress that is detrimental to epithelial biology.

Example 2

This example describes a method of using MAO inhibitors to improve hair biology, in particular, hair growth, in vivo.

Several MAO inhibitors were tested for the ability to improve hair growth using the Telogen Conversion Assay (TCA) described in, e.g., International Patent Publication No. 2000/73265. The TCA utilizes C57Bl/6 mice (Harlan Sprague Dawley, Inc., Indianapolis, Ind.), which exhibit synchronized hair growth, accompanied by melanogenesis, from approximately 40 days to 75 days following birth, to measure an agent's ability to convert follicles in telogen to anagen. The skin color of mice subjected to treatment is graded visually on a scale from zero to four (0=white skin; 1=light gray skin; 2=blue/black spots; 3=large blue/black region; 4=mostly blue/black skin). As a subject transitions from telogen to anagen, the skin color becomes darker.

Seven MAO inhibitors and two inactive metabolites of rasagiline were topically applied to C57Bl/6 mice at the dosages set forth in Table B over a period of 19 days. Triac (0.06%) was administered as a positive control. Animals were scored for hair growth on the basis of melanogenesis during the treatment period. The compounds that improved hair growth by inducing anagen are noted in Table B. Many of the compounds were tested independently up to four times and generated similar results.

TABLE B

| Chemical Name (Dose) | Type | Activity |
| --- | --- | --- |
| Selegiline Hydrochloride (1%) | Irreversible selective MAOB inhibitor | YES |
| Rasagiline mesylate (1%) | Irreversible selective MAOB inhibitor | YES |
| (R)-1-Aminoindan (1%) | Active metabolite of rasagiline | NO |
| Phenelzine (0.5%) | Nonselective MAO A/B inhibitor | YES |
| Pargyline HCL (1%) | Selective MAOB inhibitor | YES |
| Lazabemide (1%) | Reversible selective MAOB inhibitor | NO |
| Moclobemide (0.5%) | Reversible MAOA inhibitor | NO |
| 2-phenylethylamine HCL (0.5%) | MAO inhibitor | NO |
| Propionaldehyde (1%) | Inactive corrupted metabolite | NO |
| Clorgiline (1%) | Irreversible selective MAOA inhibitor | YES |

The results of the study are illustrated in FIG. 1. Robust hair growth induction was observed in response to both selegiline and the structurally-related inhibitor, rasagiline. Phenelzine, paragyline, and clorgiline also induced significant hair growth in vivo.

Figure 2:
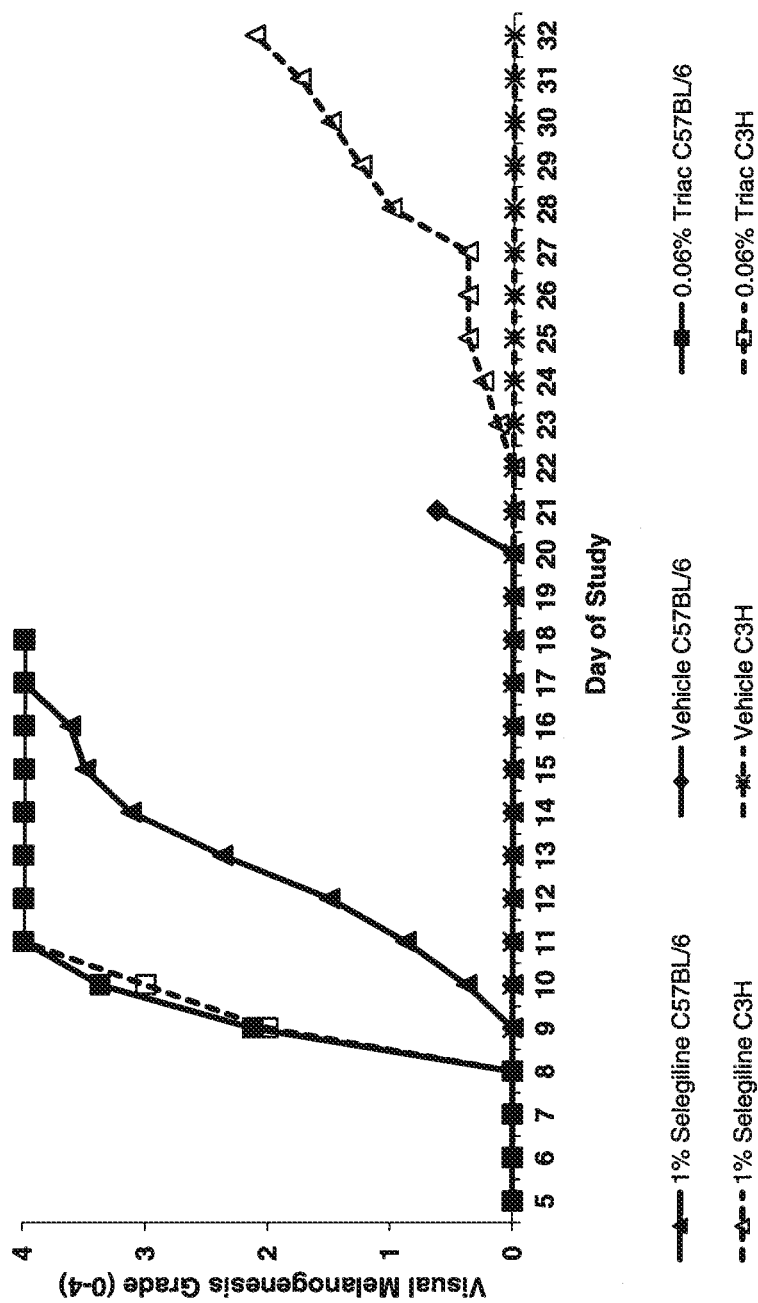
FIG. 2 is a line graph tracking hair growth (as estimated by visual melanogenesis grades (y-axis)) induced by Triac (0.06%) and selegiline (1%) in C3H and C57BL/6 mice over a treatment period of 32 days (x-axis). With Triac, a strong driver of hair growth, hair growth was induced at the same time for both mouse strains. Selegiline induced hair regrowth significantly earlier compared to that observed in subjects administered only vehicle, but the timing of selegiline-mediated induction differed between the mouse strains in a manner consistent with natural differences in hair growth rhythm in each strain.

The potential of selegiline to induce hair growth in different mouse strains also was studied. Selegiline (1%) was topically administered to a C3H mice and C57BL/6 mice. Triac (0.06%) was used as a positive control. As illustrated in FIG. 2, Triac induced hair growth simultaneously in C3H and C57BL/6 mice. Both strains of mice also responded to the MAO inhibitor; however, the strains responded in a manner consistent with natural inter-strain differences in transitioning to anagen. The telogen phase in C3H mice is longer than telogen in C57BL/6 mice. Selegiline did not override the strains' natural cycle rhythm; the transition to anagen in C3H mice occurred after the transition in C57BL/6 mice. For both strains, the MAO inhibitor initiated hair growth significantly sooner than treatment with vehicle, indicating that the MAO inhibitor works with the natural hair growth cycle to accelerate transition to anagen and improve hair growth.

The results described above reveal that MAO inhibitors improve hair growth in a clinically-relevant mouse model. MAO inhibitors work with the natural hair cycle to induce hair growth faster than negative controls, but within the natural rhythm of a particular subject.

Example 3

This example describes a method of improving hair growth by administering to a subject a MAO inhibitor and a vasodilator.

Figure 3:
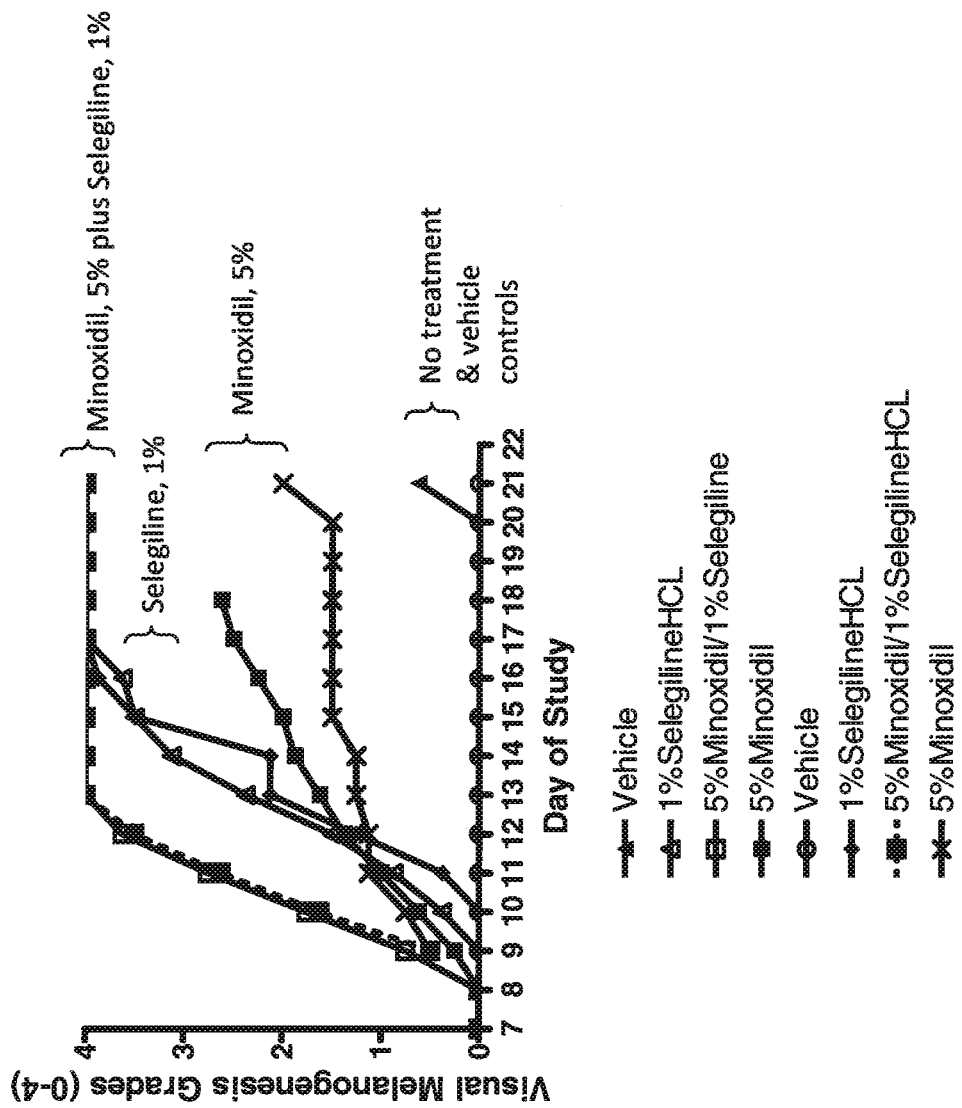
FIG. 3 is a line graph tracking hair growth (as estimated by visual melanogenesis grades (y-axis)) induced by minoxidil (5%), selegiline (1%), and a combination of minoxidil (5%) and selegiline (1%) in two independent studies of C57Bl/6 mice over a treatment period of 21 days (x-axis).
Figure 4:
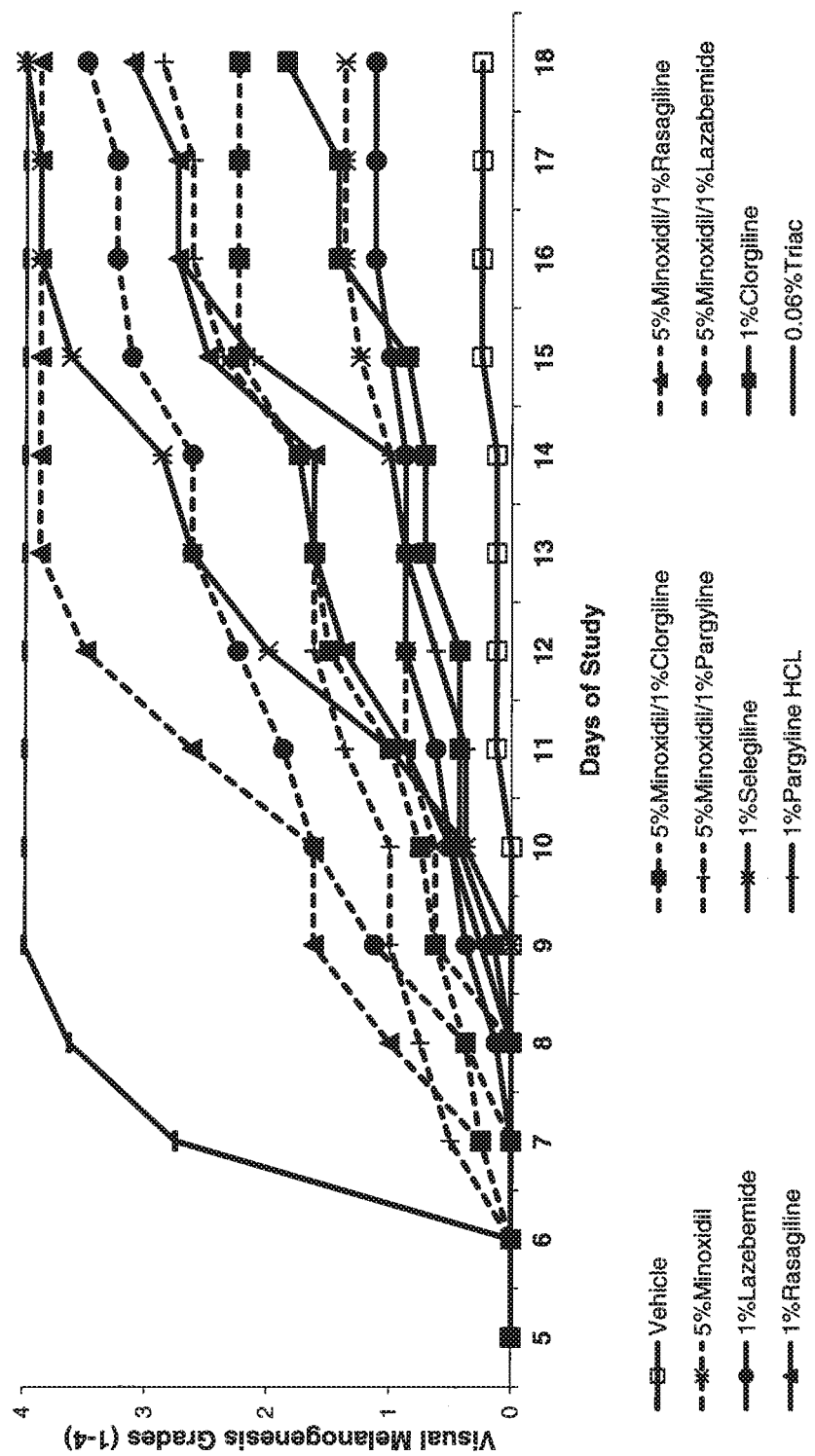
FIG. 4 is a line graph tracking hair growth (as estimated by visual melanogenesis grades (y-axis)) induced by Triac (0.06%), minoxidil (5%), lazabemide (1%), rasagiline (1%), selegiline (1%), paragyline (1%), clorgiline (1%), minoxidil (5%)+lazabemide (1%), minoxidil (5%)+rasagiline (1%), minoxidil (5%)+paragyline (1%), and minoxidil (5%)+clorgiline (1%) in C57Bl/6 mice over a treatment period of 19 days (x-axis).

A vasodilator (minoxidil, 5%) was topically administered to C57Bl/6 mice in combination with selegiline, lazebemide, rasagiline, clorgiline, or paragyline (1%), once daily for 19 days. Melanogenesis was evaluated as an indicator of hair growth using a visual scale of zero to four, as described in Example 1. The results of the study are illustrated in FIGS. 3 and 4. Administering selegiline with a vasodilator significantly improved hair growth beyond that observed following treatment with either compound alone (FIG. 3). The combination treatment accelerated the onset of hair growth compared to that observed with selegiline alone by up to two days. Combination treatment also increased the rate of hair growth in comparison to hair growth induced by minoxidil treatment alone. The results translate to an approximate 5-10% acceleration of hair growth induction in a 20 day treatment period. After 18 days of treatment, all mice administered both selegiline and minoxidil reached complete melanogenesis, while only about half of the mice administered only minoxidil (without an MAO inhibitor) reached complete melanogenesis. Two independent studies yielded the same results. A similar trend was observed with other MAO inhibitors, which also induced hair growth in combination with minoxidil in a shorter period of time and/or to a greater degree than treatment with MAO inhibitor or minoxidil alone (FIG. 4). Surprisingly, administering minoxidil with lazabemide, a reversible MAOB inhibitor not shown to induce hair growth alone, generated a strong induction of hair growth beyond that achieved with minoxidil alone.

This example demonstrates that MAO inhibitors enhance minoxidil's ability to induce hair growth. Subjects not responsive to minoxidil treatment alone responded to concurrent treatment with minoxidil and a MAO inhibitor, and the response was greater than that achieved by MAO inhibitor treatment alone. Additionally, administering an MAO inhibitor concurrently with a vasodilator significantly improved the amount of hair generated beyond the level of hair growth observed following treatment with a vasodilator or MAO inhibitor alone. In some instances, the MAO inhibitor and vasodilator were observed to function synergistically to improve hair growth, i.e., the combination treatment improved hair growth to a greater degree than the sum of the individual effects of each agent applied separately.

Example 4

A tonic of the invention is prepared by conventional methods from the following exemplary components:

| Component | wt % |
| --- | --- |
| Alcohol 100% DEB 100 (Ethanol) | 25.00 |
| Carbomer (Carbopol Ultrez 10) | 0.10 |
| BHT | 0.50 |
| Triethanolamine | 0.20 |
| Selegiline | 1 |
| Deionized water | Qs |

Example 5

A shampoo of the invention is prepared by conventional methods from the following exemplary components as described in International Patent Publication No. WO 2008/027541 and U.S. Patent Application Publication No. 20080059313:

| Component | Embodiment 1 (wt %) | Embodiment 2 (wt %) | Embodiment 3 (wt %) | Embodiment 4 (wt %) |
| --- | --- | --- | --- | --- |
| Water | Q.S. | Q.S. | Q.S. | Q.S. |
| Rheology modifying system, anionic polymer MVE/MA crosslinked copolymer | 0.05 | 0.05 | — | — |
| Rheology modifying system, clay Hydrous Na, Mg silicate (Laponite XLS) | 0.05 | 0.05 | 0.05 | — |
| Hydroxypropyl methylcellulose (PrimaFlo) | — | — | 0.10 | — |
| Polyquaternium 10 (Ucare Polymer LR-400) | 0.50 | 0.50 | 0.50 | 0.50 |
| Coconut monoethanolamide (Monamid CMA) | 1.09 | 1.03 | 1.03 | 1.50 |
| Disodium EDTA (Disslovine $Na_2S$) | 0.14 | 0.14 | 0.14 | 0.10 |
| Sodium Benzoate (Purox S Grains) | 0.25 | 0.25 | 0.25 | 0.25 |
| Sodium Citrate Dihydrate | 0.45 | 0.45 | 0.45 | 0.45 |
| Sodium Lareth-3- Sulfate (SLE3S) | 2.18 | — | — | — |
| Cocamidopropyl Betaine (Tegobetaine F-B) | 2.18 | — | — | — |
| Sodium lauryl sulfate (SLS) | 6.55 | — | — | — |
| Citric Acid | 0.08 | — | — | 0.04 |
| BHT | 0.50 | 0.50 | 0.50 | 0.50 |
| Sodium Chloride | 0.25 | 0.75 | 0.50 | 0.01 |
| Sodium Hydroxide | 0.01 | — | — | — |
| Dimethicone (Viscasil 3000,000) | 1.35 | 1.35 | 1.35 | 1.35 |
| Ammonium Laureth-3-Sulfate (AE3S) | 0.07 | 4.11 | 6.00 | 6.00 |
| Ethylene glycol distearate (EGDS) | 1.50 | 1.50 | 1.50 | 1.50 |
| Ammonium Lauryl Sulfate (ALS) | 1.50 | 6.88 | 6.88 | 10.00 |
| Methylchloroisothiazolinone & Methylisothiazolinone (Kathon CG) | 0.0005 | 0.0005 | 0.0005 | 0.0005 |
| Fragrance | 0.70 | 0.70 | 0.70 | 0.70 |
| PEG 7M (Polyox WSR-N-750) | 0.10 | — | — | 0.10 |
| DL Panthenol 50% soln. (DL-Panthenol 50L) | 0.03 | 0.03 | 0.03 | 0.03 |
| DL Panthenyl Ethyl Ether (Pantyl Ethyl Ether) | 0.03 | 0.03 | 0.03 | 0.03 |
| Lysine Monochloride | 0.03 | 0.03 | 0.03 | 0.03 |
| L-Tyrosine Methylester Hydrochloride (Methyl Tyrosine) | 0.01 | 0.01 | 0.01 | 0.01 |
| Histidine | 0.01 | 0.01 | 0.01 | 0.01 |
| Selegiline | 1.0 | 0.5 | — | — |
| Phenelzine | — | — | 1.0 | 0.5 |
| Cetyl Alcohol | | | | 0.90 |

Example 6

A conditioner of the invention is prepared by conventional methods from the following components as described in International Patent Publication No. WO 2008/027541 and U.S. Patent Application Publication No. 20080059313:

| Component | Embodiment 1 (wt %) | Embodiment 2 (wt %) | Embodiment 3 (wt %) |
| --- | --- | --- | --- |
| Dimethicone compound-1 [1] | — | 4.20 | — |
| Dimethicone compound-2 [2] | — | — | 2.00 |
| Silicone compound-2 [3] | 3.50 | — | — |
| Behenyl trimethyl ammonium chloride [6] | 2.25 | — | 3.38 |
| Isopropyl alcohol | 0.60 | — | 0.90 |
| Stearamidopropyl dimethylamine [7] | — | 2.00 | — |
| Glutamic acid [8] | — | 0.64 | — |
| Cetyl alcohol [9] | 1.90 | 2.50 | 2.30 |
| Stearyl alcohol [10] | 4.60 | 4.50 | 4.20 |
| Polysorbate-20 [11] | — | — | — |
| PPG-34 [12] | — | — | — |
| Polyalphaolefin [13] | — | — | — |
| BHT | 0.50 | 0.50 | 0.50 |
| Benzyl alcohol | 0.40 | 0.40 | 0.40 |
| Methylchloroisothiazolinone/ Methylisothiazolinone [14] | 0.0005 | 0.0005 | 0.0005 |
| Perfume | 0.35 | 0.50 | 0.35 |
| NaOH | 0.014 | — | 0.014 |
| Panthenol [15] | 0.05 | — | 0.05 |
| Panthenyl ethyl ether [16] | 0.05 | — | 0.05 |
| Hydrolyzed collagen [17] | — | 0.01 | — |
| Vitamin E [18] | — | 0.01 | — |
| Decyl Glucoside [19] | — | — | — |
| Octyl methoxycinnamate | — | 0.09 | — |
| Benzophenone-3 | — | 0.09 | — |
| Disodium EDTA | 0.13 | 0.13 | 0.13 |
| Selegiline or Phenelzine | 1.0 or 0.50 | 1.0 or 0.50 | 1.0 or 0.50 |
| Deionized water | Qs | Qs | Qs |

[1] Dimethicone/Cyclomethicone: a blend dimethicone having a viscosity of 18,000,000 mPas and cyclopentasiloxane available from GE Toshiba
[2] Dimethicone blend: a blend of dimethicone having a viscosity of 18,000,000 mPas and dimethicone having a viscosity of 200 mPas available from GE Toshiba
[3] Available from GE having a viscosity 10,000 mPas, and having following formula (I): $(R_1)_a G3_a\text{-Si}—(—OSiG_2)_n\text{-}(—OSiG_b(R_1)_{2-b})_m—O—SiG_{3-a}(Ri)_a$ (I) wherein G is methyl; a is an integer of 1; b is 0, 1 or 2, preferably 1; n is a number from about 400 to about 600; m is an integer of 0; $R_1$ is a monovalent radical conforming to the general formula $CqH_{2q}L$, wherein q is an integer of 3, and L is $—N(CH_3)_2$
[6] Behenyl trimethyl ammonium chloride/Isopropyl alcohol: Genamin KDMP available from Clariant
[7] Stearamidopropyl dimethylamine: Lexamine S-13 available from Inolex
[8] Glutamic acid: available from Ajinomoto
[9] Cetyl alcohol: Konol series available from Shin Nihon Rika.
[10] Stearyl alcohol: Konol series available from Shin Nihon Rika.
[11] Polysorbate-20: Glycosperse L-20K available from Lonza Inc.
[12] PPG-34: New Pol PP-2000 available from Sanyo Kasei.
[13] Polyalphaolefin: PureSyn 100 available from ExxonMobil Chemical Company
[14] Methylchloroisothiazolinone/Methylisothiazolinone: Kathon CG available from Rohm & Haas
[15] Panthenol: Available from Roche.
[16] Panthenyl ethyl ether: Available from Roche.
[17] Hydrolyzed collagen: Peptein 2000 available from Hormel.
[18] Vitamin E: Emix-d available from Eisai.
[19] Decyl glucoside: Plantacare 2000UP available from Cognis Japan Ltd.

Example 7

A mousse of the invention is prepared by conventional methods from the following exemplary components as described in International Patent Publication No. WO 2008/027541 and U.S. Patent Application Publication No. 20080059313:

| Component | wt % |
|---|---|
| Ethanol | 51.80 |
| Propylene glycol | 5.00 |
| Propellant P75 | 4.30 |
| Cetyl alcohol | 2.20 |
| Stearyl alcohol | 1.00 |
| Polyoxyethylene lauryl alcohol | 1.00 |
| BHT | 0.50 |
| Polysorbate 60 | 0.40 |
| Phenelzine | 1.0 |
| Acetic acid (pH 6.0) | Qs |
| Deionized water | Qs |

Example 8

An oil-in-water mascara containing large wax particles and fibers is produced using the following exemplary components:

| Phase | Components | wt % |
|---|---|---|
| A | Glyceryl Monostearate | 5.250 |
| A | Black Iron Oxide | 4.250 |
| A | Disteardimonium Hectorite | 2.250 |
| A | Stearic Acid | 2.750 |
| A | Carnauba Wax | 2.000 |
| A | Triethanolamine | 1.750 |
| A | Synthetic Wax | 1.500 |
| A | Polyvinyl Alcohol | 1.500 |
| A | Propylene Carbonate | 0.750 |
| A | Lecithin | 1.250 |
| A | Oleic Acid 80% | 1.000 |
| B | Acrylates Copolymer | 5.170 |
| B | Deionized Water | 41.58 |
| B | Simethicone Emulsion 30% | 0.200 |
| C | Xanthan Gum | 0.6 |
| C | Propylene Glycol | 3.000 |
| D | Ammonium Acrylates Copolymer | 17.79 |
| E | Ethyl Alcohol SD 40-B | 1.000 |
| E | Benzyl Alcohol | 0.650 |
| E | Panthenol | 0.280 |
| E | Phenoxyethanol | 0.280 |
| E | Methylparaben | 0.200 |
| E | Ethylparaben | 0.200 |
| E | Propylparaben | 0.100 |
| E | Trisodium EDTA | 0.100 |
| F | Fiberlon 102 DC B2 | 0.600 |
| G | 20 micrometer Polyethylene Wax Particle | 3.000 |
| G | Selegiline | 1.000 |
| TOTAL | | 100.000 |

Phase A is heated to melt the waxes and allow the pigment to be dispersed with a Cowles Blade mixer. Phase B materials are stirred together at ambient conditions, and Phase C materials are stirred together at ambient conditions and then it is added to Phase B (to gel Phase B), and the mixture is stirred and then heated to about 85 C. The Phase A and Phases B/C are mixed together to create an oil (wax) in water emulsion. The mixture is stirred for 15 minutes and then is cooled gradually till room temperature. During the cool down, Phases D and E are added to the mixture and stirred in below 60 C. Phase F is a 10 Decitex 2 mm Nylon-6 polymerized with Carbon Black (D&C Black No. 2) fiber added and mixed to homogeneity. Phase G is spherical polyethylene wax particles that are prepared separately using typical process known in the art such as spray drying. Phase G is added to and mixed with the mascara once the mascara has cooled down to about 25° C.

Example 9

An anhydrous mascara having coated hollow particles and fibers is prepared as follows:

| Phase | Component | wt % |
|---|---|---|
| A | Tall Oil Glycerides | 0.500 |
| A | Pentaerythrityl Hydrogenated Rosinate | 2.000 |
| A | Carnauba Wax | 5.000 |
| A | Polyethylene Wax | 8.500 |
| A | Trihydroxystearin | 2.500 |
| A | Propylparaben | 0.100 |
| A | BHA | 0.100 |
| A | Phenoxyethanol 99% | 0.800 |
| A | Petroleum Distillates | 62.10 |
| B | Disteardimonium Hectorite | 6.000 |
| C | Propylene Carbonate | 2.000 |
| D | Black Iron Oxide | 7.000 |
| D | NFCB-10D-2T | 0.400 |
| E | Matsumoto MFL 60CA (Calcium Carbonate coated hollow particle) | 2.000 |
| E | Selegiline | 1.000 |
| TOTAL | | 100.000 |

Phase A ingredients are melted and mixed together with low shear mixing. Phase B is gradually added to the Phase A and then dispersed with high shear mixing. Phase C is then added and mixed in with high shear mixing. The Phase D is then added and dispersed with high shear mixing. The batch is cooled to ambient conditions and the Phase E is added and mixed in.

Example 10

A skin care composition of the invention is prepared as follows:

| | Embodiment | | | | | |
|---|---|---|---|---|---|---|
| Component | A | B | C | D | E | F |
| Acrylic acid alkyl acrylate copolymer 1 [1] | | | | | | 0.2 |
| Acrylic acid alkyl acrylate copolymer 2 [2] | 0.24 | 0.24 | 0.24 | 0.24 | 0.2 | |
| Aminomethyl propanol | 0.12 | 0.12 | 0.14 | 0.12 | 0.15 | 0.1 |
| Panthenol [3] | 1.0 | 1.0 | 1.0 | 1.0 | 2.0 | 1.0 |
| Niacinamide [4] | 2.0 | 2.0 | 2.0 | 2.0 | 2.0 | 2.0 |
| Glycerin | 6.5 | 6.5 | 6.5 | 6.5 | 5.0 | 5.0 |
| 1,3-butylene glycol | 0.08 | 0.08 | 0.08 | 0.08 | 8.0 | 8.0 |
| Sodium Hyaluronate [5] | | | | | 0.02 | 0.02 |
| Isohexadecane [6] | 2.0 | | | 2.0 | 2.5 | 2.5 |
| Isododecane [7] | | 2.0 | | | | |
| Isononyl isononanoate [8] | | | 2.0 | | | |
| Dimethicone/Dimethiconol [9] | 1.5 | 1.5 | 1.5 | | 1.0 | |
| Cyclomethicone/Dimethiconol [10] | | | | 1.5 | | 1.0 |
| Xanthan gum [11] | 0.04 | 0.04 | 0.04 | 0.04 | | |
| Carbomer [12] | | | | | 0.2 | |
| Methyl Paraben | 0.15 | 0.15 | 0.15 | 0.15 | 0.15 | 0.15 |

-continued

| Component | Embodiment | | | | | |
|---|---|---|---|---|---|---|
| | A | B | C | D | E | F |
| Benzyl alcohol | 0.25 | 0.25 | 0.25 | 0.25 | 0.25 | 0.25 |
| Sodium benzoate | 0.05 | 0.05 | 0.05 | 0.05 | 0.05 | 0.05 |
| EDTA-2Na | 0.1 | 0.1 | 0.1 | 0.1 | 0.1 | 0.1 |
| Phenelzine | 1 | 0.5 | 1 | 1 | 1 | 0.5 |
| Deionized Water | | | q.s. to 100% | | | |

| Component | Embodiment | | | |
|---|---|---|---|---|
| | G | H | I | J |
| Acrylic acid alkyl acrylate copolymer 1 [1] | | | 0.1 | 0.1 |
| Acrylic acid alkyl acrylate copolymer 2 [2] | 0.4 | 0.4 | 0.3 | 0.2 |
| Aminomethyl propanol | 0.15 | 0.15 | 0.15 | 0.2 |
| Panthenol [3] | | 1.0 | 2.0 | 1.0 |
| Panthenyl ethyl ether [13] | 2.0 | 1.0 | | 2.0 |
| Niacinamide [4] | 2.0 | 2.0 | 2.0 | 3.0 |
| Glycerin | 5.0 | 5.0 | 5.0 | 8.0 |
| 1,3-butylene glycol | 5.0 | 5.0 | 5.0 | 2.0 |
| Isohexadecane [6] | 2.0 | 2.0 | | |
| Isododecane [7] | | | 3.0 | |
| Iosononyl isononanoste [8] | | | | 2.0 |
| Dimethicone/Dimethiconol [9] | 1.5 | | 1.0 | |
| Cyclomethicone/Dimethiconol [10] | | 2.0 | | 2.0 |
| Carbomer [12] | | | | 0.2 |
| Methyl Paraben | 0.15 | 0.15 | 0.15 | 0.15 |
| Benzyl alcohol | 0.25 | 0.25 | 0.25 | 0.25 |
| Sodium benzoate | 0.05 | 0.05 | 0.05 | 0.05 |
| EDTA-2Na | 0.1 | 0.1 | 0.1 | 0.1 |
| Phenelzine | 1 | 0.5 | 1 | 0.5 |
| Deionized Water | | q.s. to 100% | | |

[1] Acrylic acid alkyl acrylate copolymer 1: PEMULEN TR-1 available from B. F. Goodrich
[2] Acrylic acid alkyl acrylate copolymer 2: PEMULEN TR-2 available from B. F. Goodrich
[3] Panthenol: available from Roche
[4] Niacinamide: available from Roche
[5] Sodium Hyaluronate: available from Chisso Corp.
[6] Isohexadecane: Permethyl 101A available from Presperse
[7] Isododecane: Permethyl 99A available from Presperse
[8] Isononyl isononanoate: Salacos 99 available from Nisshin Oil Mills, or Lanol 99 available from Seppic
[9] Dimethicone/Dimethiconol: DCQ2-1403 available from Dow Corning
[10] Cyclomethicone/Dimethiconol: DCQ2-1401 available from Dow Corning
[11] Xanthan gum: Keltrol T available from Kelco
[12] Carbomer: Carbopol 981 available from B. F. Goodrich
[13] Panthenyl ethyl ether: Ethyl panthenol available from Roche Method of Production:

The polymeric materials such as the carboxylic acid/alkyl carboxylate copolymer, are dispersed in a portion of water at room temperature, mixed at a rotation speed controlled to no more than 5000 rpm, of by vigorous agitation, and heated to about 70 degrees C. until homogenous. A triblender can be used if necessary to disperse the polymeric materials. To this mixture, the silicone component and the emollient oil are added. The neutralizing agent, if present, is added to the mixture. After neutralizing, a water solution of the remaining components including tacky skin treatment agents, water soluble humectants, additional viscosity modifier, if present, and other components, if present, are added to the mixture, and then cooled to below 40 degrees C.

Embodiments A-J are useful, e.g., for providing clear lotions for use on the facial skin. When used on the facial skin, the compositions of embodiments A-J provide moisturizing benefit to the skin without leaving a tacky and/or greasy feel to the skin.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

In addition to the foregoing, the invention includes, as an additional aspect, all embodiments of the invention narrower in scope in any way than the variations specifically mentioned above. With respect to aspects of the invention described as a genus, all individual species are individually considered separate aspects of the invention. With respect to aspects of the invention described or claimed with "a" or "an," it should be understood that these terms mean "one or more" unless context unambiguously requires a more restricted meaning. With respect to elements described as one or more within a set, it should be understood that all combinations within the set are contemplated. If aspects of the invention are described as "comprising" a feature, embodiments also are contemplated "consisting of" or "consisting essentially of" the feature.

All documents cited in the Detailed Description of the Invention are, in relevant part, incorporated herein by reference; the citation of any document is not to be construed as an admission that it is prior art with respect to the invention. To the extent that any meaning or definition of a term in this document conflicts with any meaning or definition of the same term in a document incorporated by reference, the meaning or definition assigned to that term in this document shall govern.

While particular embodiments of the invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for improving hair growth in a subject in need thereof, the method comprising administering to a subject a monoamine oxidase (MAO) inhibitor selected from the group consisting of clorgiline, paragyline, lazabemide, selegiline, phenelzine, and rasagiline, and a vasodilator selected from the group consisting of minoxidil, apigenin, hydralazine, prostaglandin, and prostacyclin, in an amount effective to improve hair growth; wherein the method improves hair growth to a greater degree than administering the MAO inhibitor or the vasodilator alone; wherein the monoamine oxidase (MAO) inhibitor and the vasodilator are present in a same composition or in different compositions, and wherein the composition comprising the monoamine oxidase (MAO) inhibitor comprises from about 0.1% to about 20% of the monoamine oxidase (MAO) inhibitor, by weight of the composition, and wherein the composition comprising the vasodilator comprises from about 0.01% to about 20% of the vasodilator, by weight of the composition.

2. The method of claim 1, wherein the vasodilator is minoxidil.

3. The method of claim 1, wherein the MAO inhibitor is an MAOB inhibitor.

4. The method of claim 3, wherein the MAO inhibitor is a reversible MAOB inhibitor.

5. The method of claim 3, wherein the MAO inhibitor is an irreversible MAOB inhibitor.

6. The method of claim 1, comprising administering the MAO inhibitor and the vasodilator concurrently.

7. The method of claim 1, wherein the subject suffers from hair loss that is not associated with androgenetic alopecia.

8. The method of claim 1, wherein the subject is not responsive or minimally responsive to vasodilator treatment alone.

9. The method of claim 1, comprising topically administering the MAO inhibitor and vasodilator to the subject.

10. A kit comprising a composition comprising (a) a monoamine oxidase (MAO) inhibitor selected from the group consisting of clorgiline, paragyline, lazabemide, selegiline, phenelzine, and rasagiline, and, in the same composition or in a different composition, a vasodilator selected from the group consisting of minoxidil, apigenin, hydralazine, prostaglandin, and prostacyclin, in an amount effective to improve hair growth in a subject in need thereof, wherein the composition comprising the monoamine oxidase (MAO) inhibitor comprises from about 0.1% to about 20% of the monoamine oxidase (MAO) inhibitor, by weight of the composition, and wherein the composition comprising the vasodilator comprises from about 0.01% to about 20% of the vasodilator, by weight of the composition; and (b) instructions for applying said composition(s) to the skin of the subject; wherein the composition improves hair growth in a subject in need thereof to a greater degree than administering the MAO inhibitor or the vasodilator alone.

11. The kit of claim 10, wherein the vasodilator is minoxidil.

12. The kit of claim 10 or claim 11, wherein the MAO inhibitor is an MAOB inhibitor.

13. The kit of claim 12, wherein the MAO inhibitor is an irreversible MAOB inhibitor.

14. The kit of claim 12, wherein the MAO inhibitor is a reversible MAOB inhibitor.

15. A method for improving hair growth in a subject in need thereof, the method comprising administering to a subject a monoamine oxidase (MAO) inhibitor selected from the group consisting of clorgiline, paragyline, lazabemide, selegiline, phenelzine, and rasagiline, and a vasodilator selected from the group consisting of minoxidil, apigenin, hydralazine, prostaglandin, and prostacyclin, in an amount effective to improve hair growth; wherein the subject is not responsive or minimally responsive to vasodilator treatment alone; and wherein the monoamine oxidase (MAO) inhibitor and the vasodilator are present in a same composition or in different compositions, and wherein the composition comprising the monoamine oxidase (MAO) inhibitor comprises from about 0.1% to about 20% of the monoamine oxidase (MAO) inhibitor, by weight of the composition, and wherein the composition comprising the vasodilator comprises from about 0.01% to about 20% of the vasodilator, by weight of the composition.

16. The method of claim 15, wherein the vasodilator is minoxidil.

17. The method of claim 16, wherein the MAO inhibitor is an MAOB inhibitor.

18. The method of claim 16, wherein the MAO inhibitor is a reversible MAOB inhibitor.

19. The method of claim 16, wherein the MAO inhibitor is an irreversible MAOB inhibitor.

20. The method of claim 15, comprising administering the MAO inhibitor and the vasodilator concurrently.

21. The method of claim 20, wherein the subject suffers from hair loss that is not associated with androgenetic alopecia.

22. The method of claim 20, comprising topically administering the MAO inhibitor and vasodilator to the subject.

* * * * *